(12) United States Patent
     Thiam

(10) Patent No.: US 10,816,560 B2
(45) Date of Patent: Oct. 27, 2020

(54) METHOD FOR ANALYZING THE ABILITY OF A SUBSTANCE TO CROSS A BILAYER MEMBRANE

(71) Applicants: Paris Sciences Et Lettres—Quartier Latin, Paris (FR); Universite Paris Diderot Paris 7, Paris (FR); Centre National de la Recherche Scientifique (CNRS), Paris (FR); Sorbonne Universite, Paris (FR)

(72) Inventor: Abdou Rachid Thiam, Choisy-le-Roi (FR)

(73) Assignees: Paris Sciences Et Lettres—Quartier Latia (FR); Universite Paris Diderot Paris 7 (FR); Centre National de la Recherche Scientifique (CNRS) (FR); Sorbonne Universite (FR)

( * ) Notice: Subject to any disclaimer, the term of this patent is extended or adjusted under 35 U.S.C. 154(b) by 58 days.

(21) Appl. No.: 16/315,452

(22) PCT Filed: Jul. 4, 2017

(86) PCT No.: PCT/EP2017/066682
    § 371 (c)(1),
    (2) Date: Jan. 4, 2019

(87) PCT Pub. No.: WO2018/007408
     PCT Pub. Date: Jan. 11, 2018

(65) Prior Publication Data
     US 2019/0242914 A1    Aug. 8, 2019

(30) Foreign Application Priority Data
     Jul. 4, 2016    (EP) .................................... 16305840

(51) Int. Cl.
    *G01N 33/92*    (2006.01)
    *B01L 3/00*     (2006.01)

(52) U.S. Cl.
    CPC ........ *G01N 33/92* (2013.01); *B01L 3/502784* (2013.01); *B01L 2300/047* (2013.01); *B01L 2300/087* (2013.01); *B01L 2300/165* (2013.01)

(58) Field of Classification Search
    None
    See application file for complete search history.

(56) References Cited

PUBLICATIONS

Barriga, et al., "Droplet Interface Bilayer Reconstitution and Activity Measurement of the Mechanosensitive Channel of Large Conductance from *Escherichia coli*", Journal of the Royal Society Interface, vol. 11, No. 98, Sep. 2014, 4 pages.

(Continued)

*Primary Examiner* — Xiaoyun R Xu
(74) *Attorney, Agent, or Firm* — Lerner, David, Littenberg, Krumholz & Mentlik, LLP (57) ABSTRACT

The present invention relates to a method to analyse the ability of a substance (3) to cross a bilayer membrane comprising the following steps: (i) providing in a hydrophobic medium (1) a first droplet $D_1$ of an aqueous solution $AS_1$, wherein the droplet $D_1$ is surrounded by a monolayer of amphiphilic molecules (2), (ii) providing in the said hydrophobic medium (1) a second droplet $D_2$ of an aqueous solution $AS_2$ containing the substance (3) to be analysed, wherein the droplet $D_2$ is surrounded by a monolayer of amphiphilic molecules (2), (iii) putting the first droplet $D_1$ and the second droplet $D_2$ into contact so as to form a bilayer of amphiphilic molecules (2) in the contact area and to have a contact angle $2\theta$ between the two droplets $D_1$ and $D_2$ comprised between 10° and 180°, (iv) adding to the hydrophobic medium (1) a solvent capable of separating the droplets $D_1$ and $D_2$ put into contact, (v) collecting the droplet (Continued)

$D_1$, and (vi) analysing the content of the droplet $D_1$ in order to determine the presence or not of the substance (3).

19 Claims, 9 Drawing Sheets

(56) References Cited

PUBLICATIONS

Bayley, et al., "Droplet Interface Bilayers", Molecular Biosystems, vol. 4, No. 12, Sep. 2008, pp. 1191-1208.
International Search Report for PCT/EP2017/066682, dated Aug. 28, 2017.
Jo, et al., "Cell-Penetratng Peptide (CPP)-Conjugated Proteins is an Efficient Tool for Manipulation of Human Mesenchymal Stromal Cells", Scientific Reports, vol. 4, Mar. 2014, 8 pages.
Lein, et al., "Protein Transport Across Membranes: Comparison Between Lysine and Guanidinium-Rich Carriers", Biochimica et Biophysica Ada (BBA)-Biomembranes, vol. 1848, No. 11, Nov. 2015, pp. 2980-2984.
Schlicht and Zagnoni, "Droplet-Interface-Bilayer Assays in Microfluidic Passive Networks", Scientific Reports, Apr. 2015, 8 pages.
Thiam, et al., "From Stability to Permeability of Adhesive Emulsion Bilayers", Langmuir, vol. 28, No. 15, Apr. 2012, pp. 6291-6298.

METHOD FOR ANALYZING THE ABILITY OF A SUBSTANCE TO CROSS A BILAYER MEMBRANE

CROSS-REFERENCE TO RELATED APPLICATIONS

This application is a national phase entry under 35 U.S.C. § 371 of International Application No. PCT/EP2017/066682 filed Jul. 4, 2017, which claims the priority from European Patent Application No. 16305840.7 filed in the European Patent Office on Jul. 4, 2016, the entire contents of which are hereby incorporated by reference.

The present invention relates to a method for analyzing the ability of a substance to cross a bilayer membrane, and more particularly a biological bilayer membrane, method which can be used for performing a high-throughput screening (HTS).

In the pharmaceutical field, the ability of a drug to cross biological bilayer membranes is crucial for its activity. In particular, when the drug is administered orally, the drug has first to cross the intestinal wall to be able to reach its target. To solve this problem, drugs may be coupled with peptides able to cross these biological bilayer membranes. However, today few biological peptides are known and used. There is thus a great interest to be able to find new molecules capable of crossing biological bilayer membranes in order to help drugs to reach their target.

The main method used today for identifying molecules able to cross a biological bilayer membrane is PAMPA (Parallel Artificial Membrane Permeability Assay). Such a method uses 96 well plates comprising top and bottom phases separated by an oil phase. The two generated interfaces are covered by a phospholipid monolayer. A sample of the molecule to be tested is deposited at the aqueous top phase and after half a day or a day, the optical index of the bottom phase is measured to determine if the molecule has crossed the interphase which mimics the biological bilayer membrane. However, this method requires long experimental times to obtain a result. Furthermore, the interphase does not represent a good mimic of biological bilayer membrane giving results with a low accuracy.

Another technique uses vesicles. These vesicles have a size from hundred nanometers to few micrometers and are put in a solution containing molecules to be tested. If these molecules are able to cross a bilayer membrane, they will translocate into the vesicles. After a sufficient time, the vesicles need thus to be rapidly recovered from the surrounding aqueous phase without being damaged and contaminated by the molecules contained in the aqueous phase, which can be a difficult task, in particular due to the low stability of the vesicles.

Another technique is the so-called Caco-2 technique, which is cell-based. This method implies to form a layer of cells and to determine which substances are able to cross this layer of cells. This technique thus involves cell culture. The difficulty with this method is to form a uniform layer on the whole surface of the device used for this experiment and to always have healthy cells.

There is thus a need for new methods capable of identifying molecules able of crossing biological bilayer membranes with a shorter experimental time and a higher accuracy.

The present invention allows providing a solution to such a problem.

The present invention relates thus to a method to analyse the ability of a substance (3) to cross a bilayer membrane comprising the following steps:

(i) providing in a hydrophobic medium (1) a first droplet $D_1$ of an aqueous solution $AS_1$, wherein the droplet $D_1$ is surrounded by a monolayer of amphiphilic molecules (2), (ii) providing in the said hydrophobic medium (1) a second droplet $D_2$ of an aqueous solution $AS_2$ containing the substance (3) to be analysed, wherein the droplet $D_2$ is surrounded by a monolayer of amphiphilic molecules (2), (iii) putting the first droplet $D_1$ and the second droplet $D_2$ into contact so as to form a bilayer of amphiphilic molecules (2) in the contact area and to have a contact angle $2\theta$ between the two droplets $D_1$ and $D_2$ comprised between 10° and 180°, (iv) adding to the hydrophobic medium (1) a solvent capable of separating the droplets $D_1$ and $D_2$ put into contact, (v) collecting the droplet $D_1$, and (vi) analyzing the content of the droplet $D_1$ in order to determine the presence or not of the substance (3).

The invention will be described by way of example, with reference to the accompanying drawings.

Figure 1:
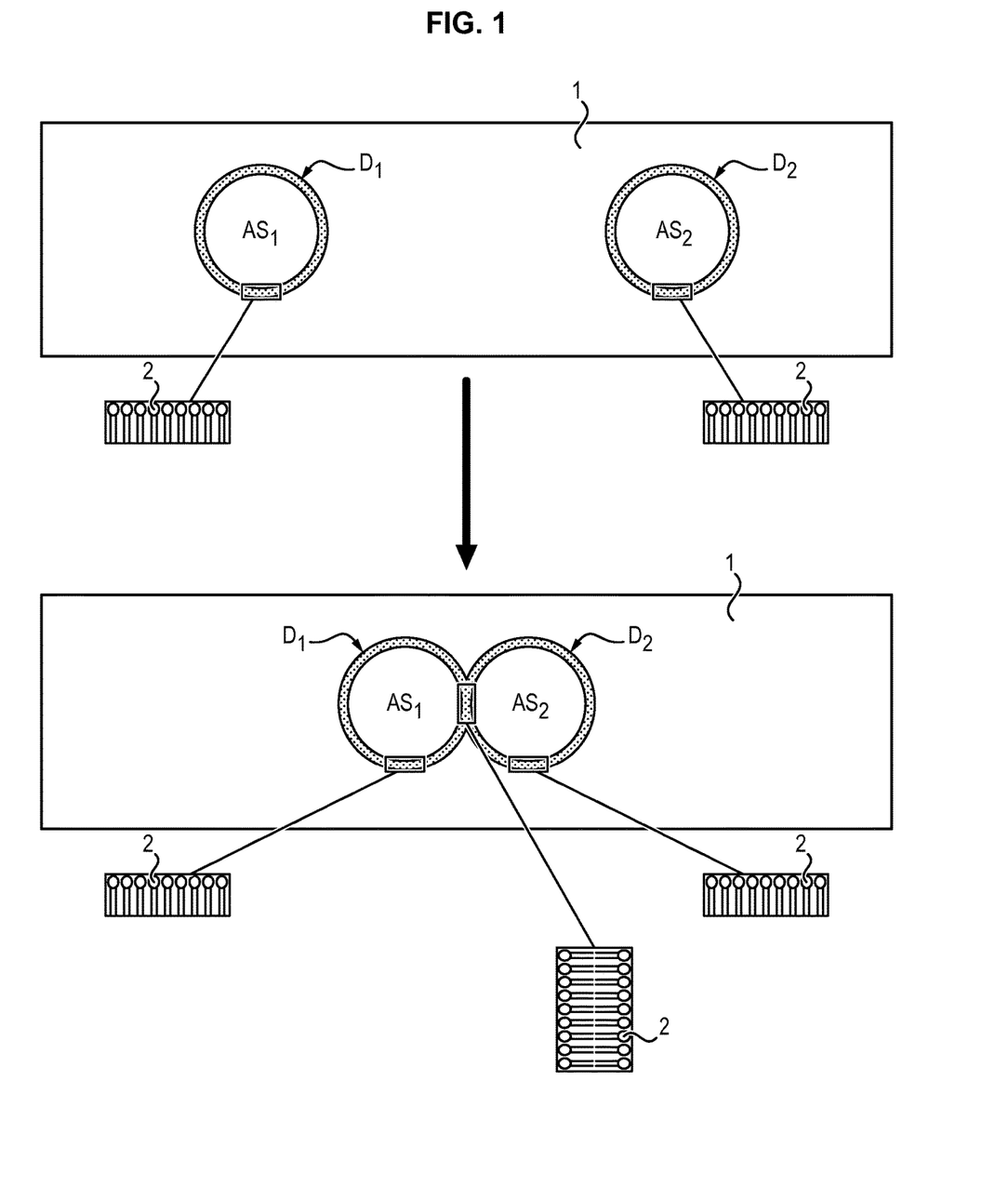
FIG. 1 illustrates step (iii) of the method according to the invention relative to the formation of the bilayer of amphiphilic molecules (2).

The bilayer of amphiphilic molecules (2) formed in step (iii) (see FIGS. 1 and 2) mimics biological bilayer membranes such as cell membranes. Consequently, a substance which is capable of crossing such a bilayer membrane will be able to cross a biological bilayer membrane. Such an ability can be determined easily with the method of the present invention. Indeed, when a substance initially present in the droplet $D_2$ (donor droplet) is found in the droplet $D_1$ (collector droplet), this means that the substance has crossed the bilayer membrane. Short times of about 1 h or less are sufficient to obtain the result which is well below the experimental times of the prior art.

Hydrophobic Medium (1):

The "hydrophobic medium" (1) according to the invention is a medium which is not miscible with water and in particular with the aqueous solutions $AS_1$ and $AS_2$ mentioned previously.

Advantageously, it can comprise an oil such as a vegetable oil (e.g. soybean oil), triglycerides (e.g. triolein, glycerol trivalerate, glyceryl trioctanoate), a silicone oil, a high molecular weight hydrocarbon (e.g. a hydrocarbon having from 10 to 40 carbon atoms such as squalene, decane, dodecane, etc.), or a mixture thereof; optionally in admixture with a solvent such as a halogenated hydrocarbon (e.g. chloroform or dichloromethane), an alcohol (e.g. butanol), an ether (e.g. diethyl ether or 1,4-dioxane), a fatty acid (e.g. oleic acid), a diglyceride (e.g. glyceryl dioctanoate or glyceryl dioleated), an ester (e.g. ethyl acetate or isopropyl acetate), a low molecular weight hydrocarbon (e.g. pentane, cyclopentane, hexane, cyclohexane, benzene or toluene), or a mixture thereof.

The hydrophobic medium (1) contains thus an oil having hydrophobic properties which can be a vegetable oil, triglycerides, a silicone oil, a high molecular weight hydrocarbon, or a mixture thereof.

"Triglycerides" (also called TG, triacylglycerol, TAG, or triacylglyceride) is an ester derived from glycerol and three fatty acids, which can be identical or different, notably identical. A triglyceride has more particularly the following formula (I):

wherein $A_1$, $A_2$ and $A_3$, identical or different, notably identical, are a hydrocarbon chain of a fatty acid. The triglycerides used in the present invention can be in the form of a mixture of various triglycerides, such as triglycerides present in a vegetable oil (for ex. soybean oil).

In the context of the present invention, "fatty acid" refers to a linear, saturated or unsaturated carboxylic acid ($RCO_2H$) comprising from 4 to 30, such as from 6 to 30, notably from 8 to 28, in particular from 10 to 24, for example from 12 to 22 carbon atoms (including the carbon atom of the carboxylic acid function). The fatty acid can have for example from 5 to 24 carbon atoms. It can be notably valeric acid, octanoic acid, capric acid, lauric acid, myristic acid, palmitic acid, staric acid, arachidic acid, myristoleic acid, myristelaidic acid, palmitoleic acid, palmitelaidic acid, oleic acid, elaidic acid, linoleic acid, linolenic acid, ecosenoic acid or arachidonic acid.

In the context of the present invention, "hydrocarbon chain of a fatty acid" refers to the hydrocarbon chain (R) linked to the acid function of the fatty acid ($RCO_2H$). R thus represents a linear, saturated or unsaturated hydrocarbon chain comprising from 3 to 29, such as from 5 to 29, notably from 7 to 27, in particular from 9 to 23, for example from 11 to 21 carbon atoms. It can be notably the hydrocarbon chain of valeric acid, octanoic acid, capric acid, lauric acid, myristic acid, palmitic acid, staric acid, arachidic acid, myristoleic acid, myristelaidic acid, palmitoleic acid, palmitelaidic acid, oleic acid, elaidic acid, linoleic acid, linolenic acid, ecosenoic acid or arachidonic acid.

By "unsaturated" is meant in the present invention that the chain comprises one or several double bonds C=C, notably one to four, such as one, two or three.

The triglycerides can be in particular triglycerides of formula (I) with $A_1$, $A_2$ and $A_3$, identical or different, notably identical, representing a linear, saturated or unsaturated hydrocarbon chain comprising from 3 to 23, such as from 4 to 24, notably from 5 to 19 carbon atoms. The triglycerides can be present in the form of a mixture of various triglycerides, such as those present in a vegetable oil, for ex. soybean oil. It can be also triolein, glycerol trivalerate or glyceryl trioctanoate.

By "high molecular weight hydrocarbon" is meant in the present invention a linear or branched, saturated or unsaturated (including aromatic) hydrocarbon containing at least 10 carbon atoms. Advantageously, the high molecular weight hydrocarbon will contain from 10 to 40 carbon atoms, such as from 15 to 30 carbon atoms, provided that the hydrocarbon is liquid at the temperature at which the method is performed, typically room temperature (i.e. from 15 to 40° C., preferably from 20 to 30° C.). It can be notably decane, dodecane, hexadecane or squalene, in particular squalene. It can be also in the form of a mixture of high molecular weight hydrocarbons such as a mineral oil.

According to a particular embodiment, the oil will be more particularly a mixture of triglyceride(s) and high molecular weight hydrocarbon(s). The high molecular weight hydrocarbon can be squalene and the triglyceride (or mixture of triglycerides) can be triglycerides of formula (I) with $A_1$, $A_2$ and $A_3$, identical or different, notably identical, representing a linear, saturated or unsaturated hydrocarbon chain comprising from 5 to 23, such as from 7 to 21 carbon atoms, such as a vegetable oil (for ex. soybean oil), triolein, glyceryl octanoate or a mixture thereof.

According to another particular embodiment, the oil will be more particularly a triglyceride or a mixture of triglycerides. The triglycerides can be in particular triglycerides of formula (I) with $A_1$, $A_2$ and $A_3$, identical or different, notably identical, representing a linear, saturated or unsaturated hydrocarbon chain comprising from 5 to 23, such as from 7 to 21 carbon atoms. It can be notably a vegetable oil (for ex. soybean oil), triolein, glyceryl octanoate or a mixture thereof.

The hydrophobic medium (1) may contain also a solvent such as a halogenated hydrocarbon (e.g. chloroform or dichloromethane), an alcohol (e.g. butanol), an ether (e.g. diethyl ether or 1,4-dioxane), a fatty acid (e.g. oleic acid), a diglyceride (e.g. glyceryl dioctanoate or glyceryl dioleated), an ester (e.g. ethyl acetate or isopropyl acetate), a low molecular weight hydrocarbon (e.g. pentane, cyclopentane, hexane, cyclohexane, benzene or toluene), or a mixture thereof; notably a halogenated hydrocarbon (e.g. chloroform or dichloromethane), an ether (e.g. diethyl ether or 1,4-dioxane), a low molecular weight hydrocarbon (e.g. pentane, cyclopentane, hexane, cyclohexane, benzene or toluene), or a mixture thereof; preferably a halogenated hydrocarbon (e.g. chloroform or dichloromethane).

The presence of a solvent allows for the rapid recruitment of the amphiphilic molecules to the droplets interfaces and thereby providing rapid stable DIB formation.

This solvent has a less hydrophobic character. Consequently, it may be present in an amount of less than 50%, preferably less than 20% (wt/wt) relatively to the total amount of the hydrophobic medium (1).

By "halogenated hydrocarbon" is meant in the sense of the present invention an hydrocarbon, which can be linear or branched, saturated or unsaturated (i.e. containing one or several double bond C═C), preferably linear or branched and saturated, in which one or more hydrogen atoms have been replaced by a halogen atom, i.e. F, Cl, Br or I, preferably Cl. The halogenated hydrocarbon is advantageously liquid at the temperature at which the method is performed, typically room temperature (i.e. from 15 to 40° C., preferably from 20 to 30° C.). The halogenated hydrocarbon is advantageously a short chain halogenated hydrocarbon, comprising advantageously 1 to 6 carbon atoms, such as 1 to 4 carbon atoms. It can be in particular chloroform, dichloromethane, dichloroethane (e.g. 1,2-dichloroethane), etc. It can be chloroform or dichloromethane. Preferably it is choloroform.

By "alcohol" is meant in the present invention a hydrocarbon in which a hydrogen atom has been replaced with an OH group. The hydrocarbon can be linear or branched, saturated or unsaturated (i.e. containing one or several double bond C═C), preferably linear or branched and saturated. The alcohol is advantageously liquid at the temperature at which the method is performed, typically room temperature (i.e. from 15 to 40° C., preferably from 20 to 30° C.). The alcohol is advantageously a short chain alcohol, comprising advantageously 1 to 12 carbon atoms, notably 1 to 6 carbon atoms, such as 1 to 4 carbon atoms. It can be also 4 to 12 carbon atoms, such as 4 to 8 carbon atoms, in particular 4 to 6 carbon atoms. It can be in particular butanol, more particularly n-butanol.

By "ether" is meant in the present invention a molecule of formula $A_4$-O-$A_5$ wherein $A_4$ and $A_5$ each represent independently of one another a monovalent linear or branched, saturated or unsaturated, preferably saturated, hydrocarbon chain or $A_4$ and $A_5$ may form together a chain, such as a divalent linear or branched, saturated or unsaturated, preferably saturated, hydrocarbon chain optionally containing another oxygen atom. The ether is advantageously liquid at the temperature at which the method is performed, typically room temperature (i.e. from 15 to 40° C., preferably from 20 to 30° C.). The monovalent or divalent hydrocarbon chain advantageously comprises 1 to 12 carbon atoms, notably 1 to 6 carbon atoms, such as 1 to 4 carbon atoms. It can be in particular diethyl ether or 1,4-dioxane. It could be also tetrahydrofurane.

The fatty acid is as defined previously. It may comprise advantageously 4 to 18 carbon atoms. It can be in particular oleic acid.

"Diglyceride" (also called DG, diacylglycerol, DAG, or diacylglyceride) is an ester derived from glycerol and two fatty acids, which can be identical or different, notably identical. A diglyceride has more particularly the following formula (II) or (III), or is a mixture thereof:

(II)

(III)

wherein $A_4$ and $A_5$, identical or different, notably identical, are a hydrocarbon chain of a fatty acid, in particular as defined previously.

The diglycerides can be in particular diglycerides of formula (II) or (III) or a mixture thereof with $A_4$ and $A_5$, identical or different, notably identical, representing a linear, saturated or unsaturated hydrocarbon chain comprising from 3 to 23, such as from 4 to 24, notably from 5 to 19 carbon atoms. The diglycerides can be notably glyceryl dioctanoate or dioleate.

By "ester" is meant in the present invention a molecule of formula $A_7$-OC(O)-$A_8$ wherein $A_7$ and $A_8$ each represent independently of one another a monovalent linear or branched, saturated or unsaturated, preferably saturated, hydrocarbon chain. The ester is advantageously liquid at the temperature at which the method is performed, typically room temperature (i.e. from 15 to 40° C., preferably from 20 to 30° C.). The monovalent hydrocarbon chain advantageously comprises 1 to 12 carbon atoms, notably 1 to 6 carbon atoms, such as 1 to 4 carbon atoms. It can be in particular ethyl acetate or isopropyl acetate.

The "low molecular weight hydrocarbon" is meant in the present invention a linear or branched, saturated or unsaturated (including aromatic) hydrocarbon containing no more than 9 carbon atoms, notably no more than 8 carbon atoms preferably no more than 7 carbon atoms. Advantageously, the low molecular weight hydrocarbon will contain from 5 to 9 carbon atoms, such as from 5 to 8 carbon atoms, notably from 5 to 7 carbon atoms, provided that the hydrocarbon is liquid at the temperature at which the method is performed, typically room temperature (i.e. from 15 to 40° C., preferably from 20 to 30° C.). It can be notably pentane, cyclopentane, hexane, cyclohexane, benzene or toluene.

The solvent used in the hydrophobic medium can be in particular pentane, cyclopentane, hexane, cyclohexane, benzene, toluene, 1,4-dioxane, diethyl ether, dichloromethane, chloroform or a mixture thereof, and preferably it is chloroform.

Amphiphilic Molecules (2):

An "amphiphilic molecule" (2) is a molecule comprising a hydrophilic part and a hydrophobic part.

The amphiphilic molecules (2) used in the present invention can be in particular lipids, such as phospholipids, glycolipids, monoglycerides, cholesterol, and mixtures thereof which are the types of lipids commonly present in cell membranes. The lipids can have a natural or synthetic origin. More particularly, the amphiphilic molecules (2) can be phospholipids optionally in mixture with glycolipids and/or cholesterol. Advantageously, the amphiphilic molecules (2) will be phospholipids optionally in mixture with cholesterol. Preferably, the amphiphilic molecules (2) will be phospholipids.

"Monoglyceride" (also called MG, acylglycerol, or acylglyceride) is an ester derived from glycerol and one fatty acid. A monoglyceride has more particularly the following formula (IV) or (V), or is a mixture thereof:

wherein $A_6$ is a hydrocarbon chain of a fatty acid, in particular as defined previously.

"Phospholipids" are amphiphilic lipids comprising a phosphoric acid mono- or di-ester moiety as hydrophilic part. They can have a natural or synthetic origin. Preferably, synthetic phospholipids will be used. They can be a phosphatidylcholine (PC), a phosphatidylethanolamine (PE), a phosphatidylglycerol (PG), a phosphatidylserine (PS), a phosphatidic acid (PA), a phosphatidylinositol (PI), or a mixture thereof. Preferably, it is a PC, a PE, a PG, a PS or a mixture thereof. These phospholipids have more particularly the following formula (II):

wherein:
$X^+$ is a counterion, and more particularly a monovalent cation such as $Na^+$ or $NH_4^+$,
n is 0 (i.e. $X^+$ is absent) or 1 (i.e. $X^+$ is present),
$R_1$ and $R_2$, identical or different, preferably identical, are a hydrocarbon chain of a fatty acid (as defined above), and
$R_3$ is:

and n=0 (the phospholipid is thus a PC), or and n=0 (the phospholipid is thus a PE), or and n=1 (the phospholipid is thus a PG), or and n=1 (the phospholipid is thus a PS), or with n=1 and $Y^+$ is a counterion, and more particularly a monovalent cation such as $Na^+$ or $NH_4^+$ (the phospholipid is thus a PA), or and n=1 (the phospholipid is thus a PI).

These phospholipids can be obtained from Avanti Polar Lipids.

Phospholipids formed with fatty acids having at least 12 carbon atoms (i.e. with a hydrocarbon chain having at least 11 carbon atoms) offer better stability to the droplets. Advantageously, phospholipids are formed with fatty acids having 12 to 24 carbon atoms, notably 14 to 22 carbon atoms, such as 16 to 20 carbon atoms. Preferred phospholipids are those comprising a C18 fatty acid (i.e. with a hydrocarbon chain comprising 17 carbon atoms) such as oleic acid.

In particular the phospholipids will be a PC, a PE, a PS, a PG, or a mixture thereof, advantageously formed with fatty acids having 12 to 24 carbon atoms, notably 14 to 22 carbon atoms, such as 16 to 20 carbon atoms, such as DOPC (dioleoylphosphatidylcholine), DPPC (dipalmitoylphosphatidylcholine), DOPE (dioleoylphosphatidylethanolamine), DOPS (dioleoylphosphatidylserine notably as a sodium salt), DOPG (dioleoylphosphatidylglycerone notably as a sodium salt) or a mixture thereof.

According to a first embodiment, amphiphilic molecules (2) according to the present invention will be a mixture of:
  at least one PS or PG (i.e. a PS, a PG, a mixture of PSs, a mixture of PGs or a mixture thereof), phospholipids which facilitate the translocation of a substance such as a peptide through the bilayer (notably by Coulomb's interactions), (preferably it is at least one PG)
  at least one PC (i.e. a PC or a mixture of PCs), which stabilises the bilayer, and
  at least one PE (i.e. a PE or a mixture of PEs), which stabilises the DIB.

According to a second embodiment, the amphiphilic molecules (2) according to the present invention will have the following composition:
  15 wt % to 50 wt % of PS, PG, or a mixture of PS and PG (i.e. a PS, a PG, a mixture of PSs, a mixture of PGs or a mixture thereof), preferably of PG (i.e. a PG or a mixture of PGs), 1 wt % to 70 wt % of PC (i.e. a PC or a mixture of PCs), and 1 wt % to 40 wt % of PE (i.e. a PE or a mixture of PEs).

Thus, the amphiphilic molecules (2) according to the present invention will be advantageously a mixture of at least one PC, at least one PE and at least one PS or PG, preferably a mixture of at least one PC, at least one PE and at least one PG.

In the two above mentioned embodiments for the amphiphilic molecules (2), the phospholipids (PS, PG, PC and PE) are advantageously formed with fatty acids having 12 to 24 carbon atoms, notably 14 to 22 carbon atoms, such as 16 to 20 carbon atoms, in particular 18 carbon atoms. The amphiphilic molecules (2) can be in particular a mixture of DOPC (dioleoylphosphatidylcholine), DOPE (dioleoylphosphatidylethanolamine), and DOPS (dioleoylphosphatidylserine notably as a sodium salt) and/or DOPG (dioleoylphosphatidylglycerone notably as a sodium salt), such as a mixture of DOPC (dioleoylphosphatidylcholine), DOPE (dioleoylphosphatidylethanolamine) and DOPG (dioleoylphosphatidylglycerone notably as a sodium salt).

Substance (3) to be Analyzed:

The substance to be analysed can be any substance which could be used for example in the pharmaceutical field as a vehicle to improve the ability of a drug to cross the biological bilayer membranes. It can be a molecule or a salt thereof, a complex, etc. According to a particular embodiment, the substance to be analyzed will be a peptide.

Droplets:

Advantageously, the droplets have a diameter comprised between 0.5 µm and 1000 µm, notably comprised between 20 µm and 500 µm, and preferably comprised between 50 µm and 200 µm. The droplets have thus substantially a spherical form.

The diameter of the droplets can be measured by a brightfield camera.

According to a preferred embodiment, the droplets $D_1$ and $D_2$ have substantially the same size, i.e. that the diameter $d_1$ of the droplet $D_1$ and the diameter $d_2$ of the droplet $D_2$ should advantageously satisfied the following equation:

$$|d_1-d_2|/(d_1+d_2) \leq 0.9, \text{ notably } \leq 0.5, \text{ preferably } \leq 0.2.$$

The aqueous solutions $AS_1$ and $AS_2$ will advantageously comprise a buffering agent in order to maintain the desired pH in these aqueous solutions. Advantageously, the pH of these aqueous solutions $AS_1$ and $AS_2$ will be maintained between 6 and 8, notably around about 7. The buffering agent can be for example HEPES (4-(2-hydroxyethyl)-1-piperazine-ethanesulfonic acid).

The aqueous solution $AS_2$ will further contain the substance (3) to be analyzed. The concentration of the substance (3) in the aqueous solution $AS_2$ is advantageously comprised between 1 nM and 10 mM, notably between 1 µM and 100 µM.

It could be envisaged to add a coloring agent (e.g. a fluorescent agent such as rhodamine) soluble in water to one of these aqueous solutions (i.e. $AS_1$ or $AS_2$) in order to visually distinguish droplets $D_1$ and $D_2$.

According to a particular embodiment, $AS_1$ comprises, notably consists in, water, a buffering agent and optionally a coloring agent and $AS_2$ comprises, notably consists in, water, a buffering agent, the substance (3) to be analysed and optionally a coloring agent.

Figure 2:
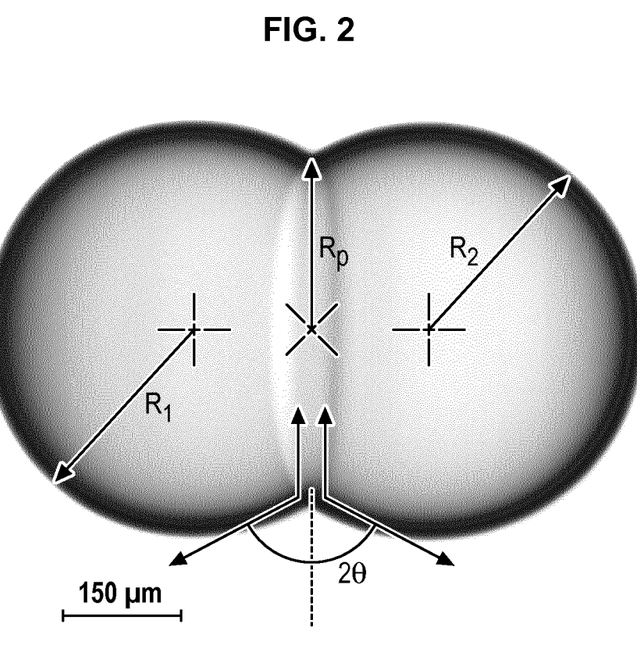
FIG. 2 illustrates the contacted droplets $D_1$ and $D_2$ obtained in step (iii).
Figure 3:
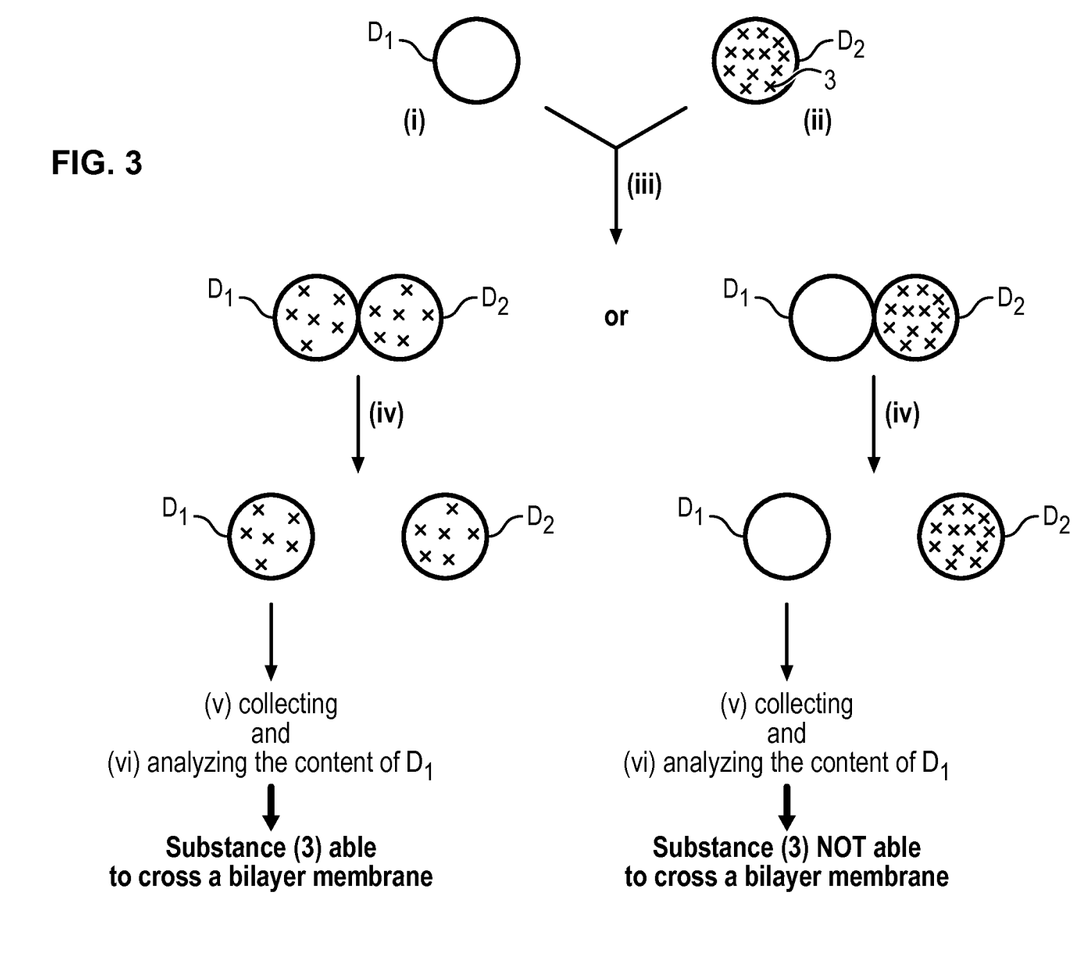
FIG. 3 illustrates the whole method according to the invention, only droplets $D_1$ and $D_2$ and the substance (3) to be tested being represented.

FIG. 2 represents $D_1$ and $D_2$ droplets after contacting, forming thus a bilayer of amphiphilic molecules (2). The main parameters of this pair of droplets are: $R_1=d_1/2$ which is the radius of the $D_1$ droplet; $R_2=d_2/2$ which is the radius of the $D_2$ droplet; $R_p$ which is the radius of the bilayer area; and $2\theta$ which is the contact angle and is calculated as follows:

$$2\theta=\sin^{-1}(R_p/R_1)+\sin^{-1}(R_p/R_2).$$

The various radii ($R_p$, $R_1$ and $R_2$) can be measured by a brightfield high-speed camera.

Advantageously, the contact angle $2\theta$ is comprised in particular between 50° and 180°, such as between 90° and 180°, notably between 120° and 180°.

Having higher contact angles is advantageous as the bilayer area (also called droplet interface bilayer (DIB)) will be higher and the translocation time will be decreased.

The contact angle can be controlled by various ways.

The nature of the hydrophobic medium (1) can have an influence on the contact angle. Indeed, the hydrophobic medium (1) advantageously comprises an oil optionally in admixture with a solvent having a less hydrophobic character. The contact angle can be increased by decreasing the content of the solvent in the hydrophobic medium (1). The nature of the amphiphilic molecules (2) can also have an impact on the contact angle. Indeed, cylinder or cone-shape like phospholipids such as PC and PI will favour higher contact angles, while inverse cone-shape like phospholipids such as PE will favour smaller contact angles. Moreover, the contact angle will also be influenced by the saturated or unsaturated nature of the amphiphilic molecules (2) such as phospholipids, higher contact angles being obtained with saturated molecules such as saturated phospholipids.

Moreover, the nature of the aqueous solutions $AS_1$ and $AS_2$, such as their pH of their ionic strength, can also modify the contact angle. For example, aqueous droplets containing divalent ions such as $Mg^{2+}$ will favour stability and high contact angles.

Solvent:

The solvent capable of separating the droplets $D_1$ and $D_2$ put into contact for example can be selected from a halogenated hydrocarbon (e.g. chloroform or dichloromethane), an alcohol (e.g. butanol), an ether (e.g. diethyl ether or 1,4-dioxane), a fatty acid (e.g. oleic acid), a diglyceride (e.g. glyceryl dioctanoate or glyceryl dioleated), an ester (e.g. ethyl acetate or isopropyl acetate), a low molecular weight hydrocarbon (e.g. pentane, cyclopentane, hexane, cyclohexane, benzene or toluene), or a mixture thereof; notably a halogenated hydrocarbon (e.g. chloroform or dichloromethane), an ether (e.g. diethyl ether or 1,4-dioxane), a low molecular weight hydrocarbon (e.g. pentane, cyclopentane, hexane, cyclohexane, benzene or toluene), or a mixture thereof; preferably a halogenated hydrocarbon (e.g. chloroform or dichloromethane), as defined previously.

According to a particular embodiment, it will be a halogenated hydrocarbon, and more particularly chloroform.

Step (i):

The droplet $D_1$ surrounded by a monolayer of amphiphilic molecules (2) can be provided by forming a droplet of the aqueous solution $AS_1$ in the hydrophobic medium (1) which contains the amphiphilic molecules (2). The amphiphilic molecules (2) will then spontaneously place themselves at the interface between the aqueous droplet and the hydrophobic medium (1).

Preferably, in this step, the volume of the hydrophobic medium (1) is at least twice the volume of the aqueous solution $AS_1$ used to form the droplets.

The concentration of the amphiphilic molecules (2) in the hydrophobic medium (1) is advantageously at least 0.025% (w/w).

Step (ii):

The droplet $D_2$ surrounded by a monolayer of amphiphilic molecules (2) can be provided by forming a droplet of the aqueous solution $AS_2$ in the hydrophobic medium (1) which contains the amphiphilic molecules (2). The amphiphilic molecules (2) will then spontaneously place themselves at the interface between the aqueous droplet and the hydrophobic medium (1).

Preferably, in this step, the volume of the hydrophobic medium (1) is at least twice the volume of the aqueous solution $AS_2$ used to form the droplets.

The concentration of the amphiphilic molecules (2) in the hydrophobic medium (1) is advantageously at least 0.025% (w/w).

Step (iii):

The two droplets $D_1$ and $D_2$ are brought into contact by any means (for ex. by mixing binary droplets or by changing the flow rate in microfluidics) used in the art. Generally, droplets $D_1$ and $D_2$ are formed separately in a hydrophobic medium (1) before merging together the two hydrophobic media (1) containing respectively droplets $D_1$ and $D_2$. A microfluidic device can also be used to generate and put into contact the droplets as detailed hereafter.

The droplets $D_1$ and $D_2$ are maintained into contact during a sufficient time to allow a substance to cross the bilayer of amphiphilic molecules (2). Advantageously, the droplets are maintained into contact during at least 1 min, notably between 1 and 180 min, such as between 5 and 60 min, in particular between 10 and 30 min.

Step (iv):

The two droplets $D_1$ and $D_2$ which are into contact are then separated by the addition of an appropriate solvent.

Such a solvent capable of separating droplets $D_1$ and $D_2$ put into contact can be for example a halogenated hydrocarbon (e.g. chloroform or dichloromethane), an alcohol (e.g. butanol), an ether (e.g. diethyl ether or 1,4-dioxane), a fatty acid (e.g. oleic acid), a diglyceride (e.g. glyceryl dioctanoate or glyceryl dioleated), an ester (e.g. ethyl acetate or isopropyl acetate), a low molecular weight hydrocarbon (e.g. pentane, cyclopentane, hexane, cyclohexane, benzene or toluene), or a mixture thereof; notably a halogenated hydrocarbon (e.g. chloroform or dichloromethane), an ether (e.g. diethyl ether or 1,4-dioxane), a low molecular weight hydrocarbon (e.g. pentane, cyclopentane, hexane, cyclohexane, benzene or toluene), or a mixture thereof; preferably a halogenated hydrocarbon (e.g. chloroform or dichloromethane), as defined previously.

According to a particular embodiment, it will be a halogenated hydrocarbon, and more particularly chloroform.

Steps (v) and (vi):

Once the droplets separated, droplet(s) $D_1$ is/are collected to be analysed. In order to collect droplet(s) $D_1$, a coloring agent can be present in the aqueous solution $AS_1$ or $AS_2$ in order to distinguish droplets $D_1$ and $D_2$. When a microfluidic device is used as detailed below, it will be possible to generate alternatively droplets $D_1$ and $D_2$ so that droplets $D_1$ will be easily collected by collecting every second droplets.

Once the droplet(s) $D_1$ is/are collected, the content of the droplet(s) $D_1$ can be analysed to determine if the substance (3) is present and has thus been able to cross the bilayer of amphiphilic molecules (2) mimicking a cell membrane so as to move from droplet $D_2$ to droplet $D_1$.

Such an analysis can be performed by any usual analytical means used notably in chemistry or biochemistry. Such an analysis can be performed by fluorescence imaging if the substance is fluorescent or react with a target which becomes fluorescent when they are in contact, such a target being present in this case in the aqueous solution $AS_1$. Otherwise, such an analysis can be performed for example by mass spectrometry or by high performance liquid chromatography (HPLC).

Microfluidic Device:

The method according to the invention can be performed in high-throughput, in particular in a HTS method.

Figure 4A:
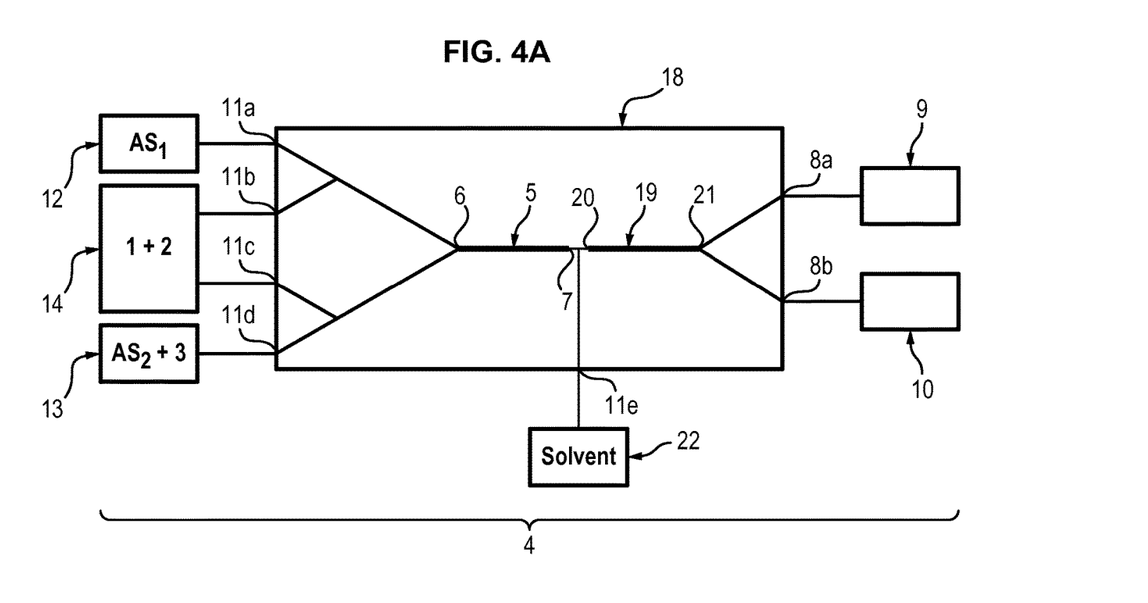
FIGS. 4A and 4B illustrate various embodiments of a microfluidic device (18) according to the invention useful to perform the method according to the invention in a high-throughput manner.
Figure 4B:
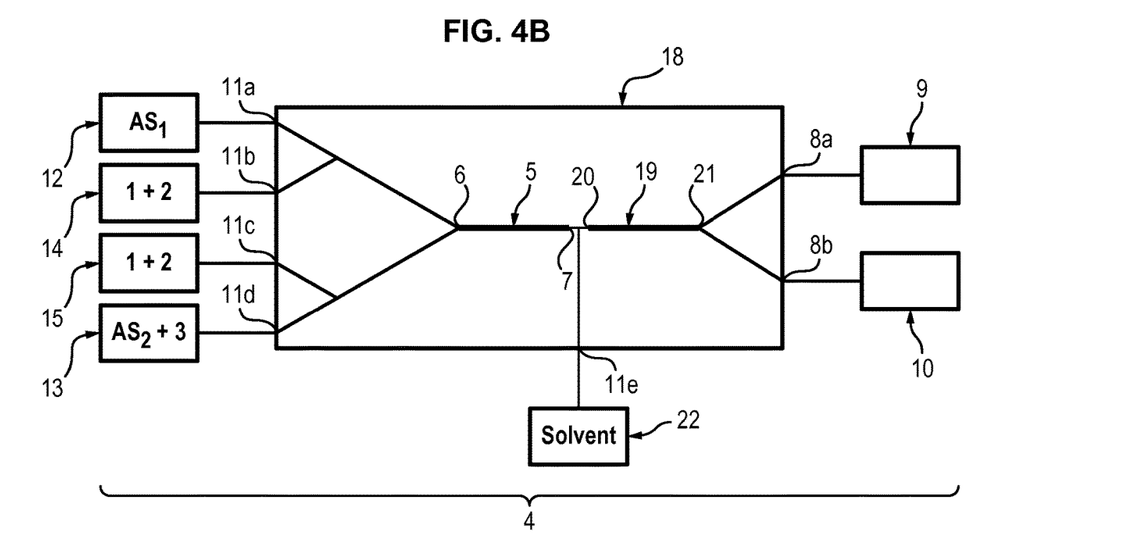

Such a high-throughput method can be performed by the use of a microfluidic analysis system (4). Such an analysis system (4) could comprise:

a microfluidic device (18) comprising:
  a first microfluidic channel (5) comprising one inlet (6) and one outlet (7), through which alternate droplets $D_1$ and $D_2$ can flow in the hydrophobic medium (1) from the inlet (6) to the outlet (7) of the first microfluidic channel (5) and can be put into contact,
  a second microfluidic channel (19) comprising one inlet (20) and one outlet (21), through which the droplets $D_1$ and $D_2$ can flow in the hydrophobic medium (1) from the inlet (20) to the outlet (21) of the second microfluidic channel (19) and the droplets $D_1$ and $D_2$ put into contact can be separated, the inlet (20) of the second microfluidic channel (19) being connected to the outlet (7) of the first microfluidic channel (5),
  at least two outlets (8a,8b) connected to the outlet (21) of the second microfluidic channel (19), wherein:
    the first outlet (8a) of the microfluidic device (18) is further connected to a first receiver container (9) intended to receive the droplets $D_1$ to be analysed, and
    the second outlet (8b) of the microfluidic device (18) is further connected to a second receiver container (10) intended to receive the droplets $D_2$,
  at least five inlets (11a,11b,11c,11d,11e):
    wherein four inlets (11a,11b,11c,11d) of the microfluidic device (18) are connected to the inlet (6) of the first microfluidic channel (5), the first two inlets (11a,11b) being further connected respectively to a reservoir (12) intended to contain the aqueous solution $AS_1$ and to a reservoir (14) intended to contain the hydrophobic medium (1) and the amphiphilic molecules (2), and
    the last two inlets (11c,11d) being further connected respectively to a reservoir (13) intended to contain the aqueous solution $AS_2$ and the substance (3) and to a reservoir (14 or 15) intended to contain the hydrophobic medium (1) and the amphiphilic molecules (2), and
    wherein one inlet (11e) of the microfluidic device (18) is connected to the inlet (20) of the second microfluidic channel (19) and is further connected to a reservoir (22) intended to contain the solvent capable of separating the droplets $D_1$ and $D_2$ put into contact,
at least four reservoirs adapted for containing respectively (i) the aqueous solution $AS_1$ (reservoir 12), (ii) the aqueous solution $AS_2$ and the substance (3) (reservoir 13), (iii) the hydrophobic medium (1) and the amphiphilic molecules (2) (reservoir(s) 14, 15), and (iv) the solvent capable of separating the droplets $D_1$ and $D_2$ put into contact (reservoir 22),
at least two receiver containers (9,10) adapted for receiving respectively (i) the droplets $D_1$ to be analyzed, and (ii) the droplets $D_2$, and
an analyzing device (17) to analyze the content of droplets $D_1$.

By "microfluidic channel" ((5) or (19)) is meant in the present invention a channel having a cross section which has dimensions in the micrometer range. Typically, the microfluidic channel will have a width and a depth comprised between 10 μm and 1000 μm, in particular between 10 μm and 400 μm, notably between 10 μm and 250 μm, preferably between 10 and 100 μm or between 150 and 250 μm. However, the length of the microfluidic channel can be in the centimeter, decimeter or even meter range.

Droplets $D_1$ are formed in the microfluidic device (18) by any means from the aqueous solution $AS_1$ (contained in a first reservoir (12)) and the hydrophobic medium (1) containing the amphiphilic molecules (2) (contained in a second reservoir (14)) which enter the microfluidic device (18) through its first and second inlets (11a,11b). Once formed, droplets $D_1$ flow in the hydrophobic medium (1) until the inlet (6) of the first microfluidic channel (5). Droplets $D_1$ can be formed for example by shearing a flow of aqueous solution $AS_1$ with two flows of hydrophobic medium (1) containing the amphiphilic molecules (2), method well-known to the one skilled in the art. The monolayer of amphiphilic molecules (2) is then formed spontaneously around the droplets $D_1$.

Droplets $D_2$ are formed similarly in the microfluidic device (18) by any means from the aqueous solution $AS_2$ containing the substance (3) (contained in a third reservoir (13)) and the hydrophobic medium (1) containing the amphiphilic molecules (2) (contained in the second reservoir (14) or a fourth reservoir (15)) which enter the microfluidic device (18) through its third and fourth inlets (11c,11d). Once formed, droplets $D_2$ flow in the hydrophobic medium (1) until the inlet (6) of the first microfluidic channel (5). Droplets $D_2$ can be formed for example by shearing a flow of aqueous solution $AS_2$ containing the substance (3) with two flows of hydrophobic medium (1) containing the amphiphilic molecules (2), method well-known to the one skilled in the art. The monolayer of amphiphilic molecules (2) is then formed spontaneously around the droplets $D_2$.

Advantageously, droplets $D_1$ and $D_2$ enter alternately the first microfluidic channel (5) through its inlet (6) and flow through this first microfluidic channel (5) from its inlet (6) to its outlet (7). Pairs of droplets $D_1$ and $D_2$ are brought into contact in this first microfluidic channel (5), for ex. by varying the pressure/flow rate in the first microfluidic channel (5), so as to form the bilayer of amphiphilic molecules (2) in the contact area. The pairs of droplets $D_1$ and $D_2$ will flow and be maintained into contact through this first microfluidic channel (5) until the end of this microfluidic channel (5).

Then, the pairs of droplets $D_1$ and $D_2$ enter a second microfluidic channel (19) through its inlet (20) and flow through this second microfluidic channel (19) from its inlet (20) to its outlet (21). A solvent capable of separating the droplets $D_1$ and $D_2$ put into contact (contained in another reservoir (22)) is introduced in the microfluidic device (18) by a fifth inlet (11e) by any means. This solvent enters the second microfluidic channel (19) through its inlet (20) in order to separate the pairs droplets $D_1$ and $D_2$ put into contact in the second microfluidic channel (19). Droplets $D_1$ and $D_2$ get out alternately of the second microfluidic channel (19) through its outlet (21) so that it is possible to direct droplets $D_1$ towards the first outlet (8a) of the microfluidic device (18) and to direct droplets $D_2$ towards the second outlet (8b) of the microfluidic device (18). Droplets $D_1$ are thus collected in a first receiver container (9), whereas droplets $D_2$ are collected in a second receiver container (10).

It is thus easy with such a device to collect separately droplets $D_1$ by collecting each second droplet.

The content of the collected droplets $D_1$ is then analyzed by means of an analyzing device (17) to determine the presence or not of the substance (3) in the droplet $D_1$. The analyzing device (17) can be any usual analytical device, notably usually used in chemistry or in biochemistry. Such an analyzing device (17) can be a device for fluorescence imaging if the substance (3) is fluorescent or react with a target which becomes fluorescent when they are in contact, such a target being present in this case in the aqueous solution $AS_1$. Otherwise, such an analyzing device (17) can be a mass spectrometer or a high performance liquid chromatography (HPLC).

When the substance (3) is detected in the content of droplet $D_1$, it can be concluded that this substance (3) is able to cross a bilayer membrane since this substance has been able to move from droplet $D_2$ to droplet $D_1$ through the bilayer of amphiphilic molecules (2).

On the contrary, when the substance (3) is not detected in the content of droplet $D_1$, it can be concluded that this substance (3) is not able to cross a bilayer membrane since this substance has not been able to move from droplet $D_2$ to droplet $D_1$ through the bilayer of amphiphilic molecules (2).

Various embodiments of such a microfluidic device (18) useful in a microfluidic analysis system (4) according to the invention are illustrated on FIGS. 4A and 4B.

Such a microfluidic analysis system (4) will allow forming and analysing numerous pairs of droplets with an automated treatment of the results. In order to perform HTS, it will be possible to introduce various substances (3) to be analyzed in aqueous solution $AS_2$. An analysis of the content of droplets $D_1$ obtained at the end of the experiment will allow the identification of the substances (3) able to cross a bilayer membrane.

The present invention will be illustrated by the following non-limiting examples.

EXAMPLES

Oils (triolein, glyceryl octanoate) and solvents (chloroform) were purchased from Sigma Aldrich. Phospholipids (DOPC, DOPE and DOPG) and fluorescent phospholipids (rhodamine-PE) were purchased from Avanti Polar Lipids. Cyclosporine was purchased from Sigma Aldrich and penetratin-gfp was purified from bacteria (Jo et al. *Sci Rep.* 2014 Mar. 14; 4:4378). All salts and Hepes were also purchased from Sigma Aldrich. Triolein-pyrene (fluorescent triglyceride) was purchased from Marker Genes.

Preparation of a phospholipid-oil mixture (hydrophobic medium containing phospholipids): 15 μl of DOPC at 25 mg/ml, 7 μl of DOPE at 25 mg/ml, 7 μl DOPG at 25 mg/ml in chloroform were mixed dried under vacuum. 400 μl of glyceryl trioctanoate were then added to obtain the hydrophobic medium with a phospholipid concentration at roughly 0.2% (w/w).

Glyceryl trioctanoate can be replaced with trioelin.

When trioelin was used instead of trioctanoate, 5% of triolein can be replaced with triolein-pyrene which is fluorescent after excitation by UV, in order to detect the optional presence of hydrophobic medium inside the droplet interface bilayer (DIB). For all solutions, 15% (v/v) chloroform was added and the solutions were put under closed vials.

Buffer solution: a buffer solution was prepared by mixing Hepes (25 mM in water), $MgCl_2$ (2 mM in water) and potassium acetate (120 mM in water).

Preparation of the aqueous solution $AS_1$: $AS_1$ corresponds to the Buffer solution.

Preparation of the aqueous solution $AS_2$ containing a peptide: $AS_2$ is prepared by adding the peptide (cyclosporine or penetratin-gfp resp. 1 µM and 10 µM) to the Buffer solution.

Bulk experiment (unless specified, the oil used is glyceryl trioctanoate)

Two populations of water-in-oil droplets (blank droplets $D_1$ and peptide-containing droplets $D_2$) are prepared separately. 10 µl of $AS_1$ solution was mixed with 150 µl of the phospholipid-oil solution and thoroughly vortexed to generate droplets $D_1$ surrounded by a phospholipid layer. The same operation is conducted to generate droplets $D_2$ surrounded by a phospholipid layer from 10 µl of $AS_2$ solution containing a peptide and 150 µl of the phospholipid-oil solution.

In a Lab-Tek™ chamber, 100 µl of the water-in-oil droplets $D_1$ population are placed and 20 µl of the water-in-oil droplets $D_2$ population are added. Then pairs of droplets $D_1$ and $D_2$ forming DIBs (i.e. into contact) are localized.

When the peptide is penetratin-gfp, i.e. a fluorescent peptide, the pairs of droplets $D_1$ and $D_2$ can be followed over time by fluorescence imaging to study the passage of the peptide from droplets $D_2$ to droplets $D_1$.

Figure 5:
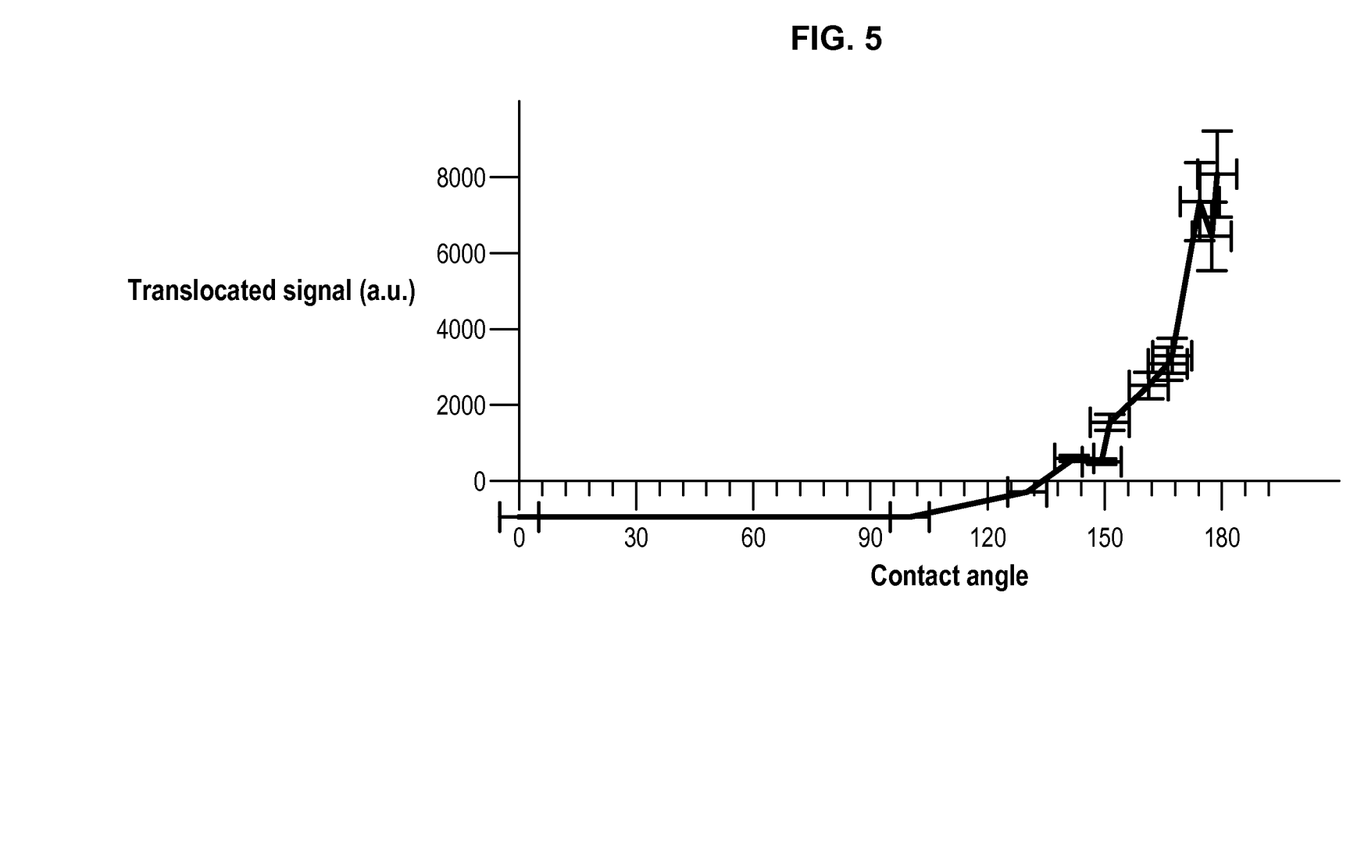
FIG. 5 represents the translocated signal of a peptide (i.e. the passage of a peptide from droplets $D_2$ to droplets $D_1$) in function of the contact angle.
Figure 6:
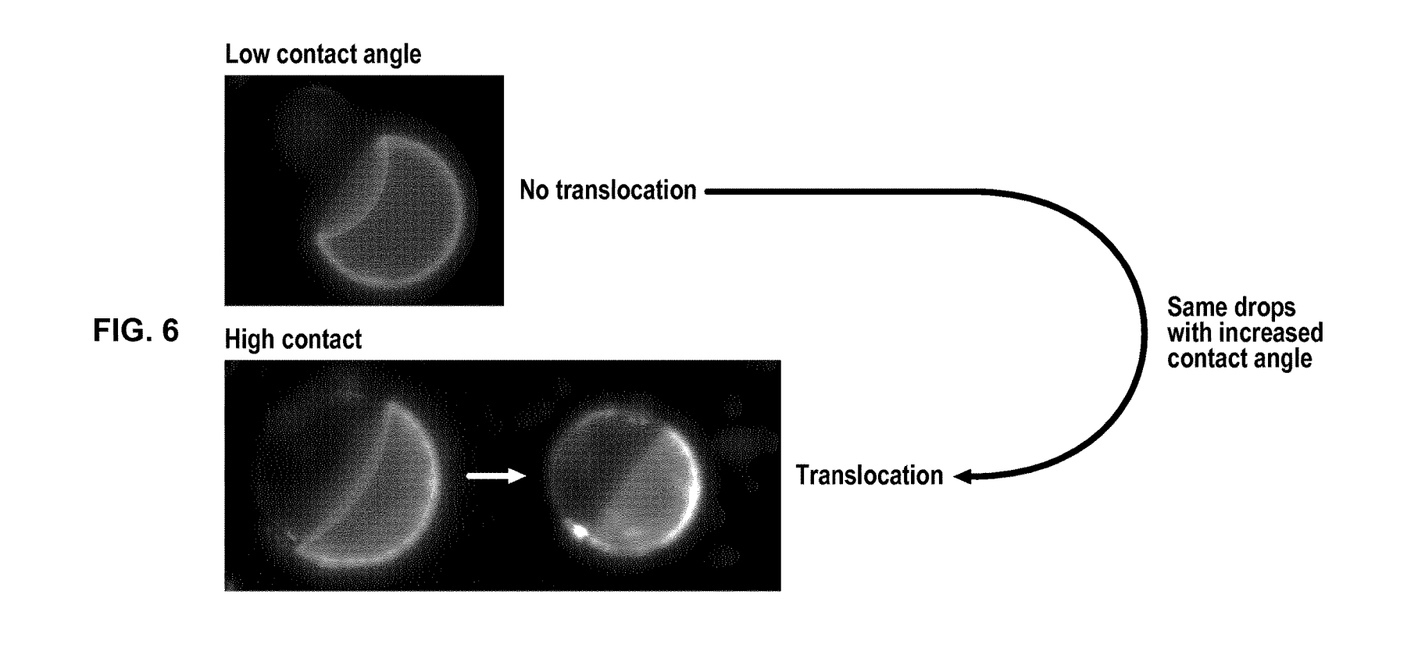
FIG. 6 represents photographs of a pair of droplets $D_1$ and $D_2$ with low or high contact angle, $D_1$ containing a fluorescent peptide.
Figure 7:
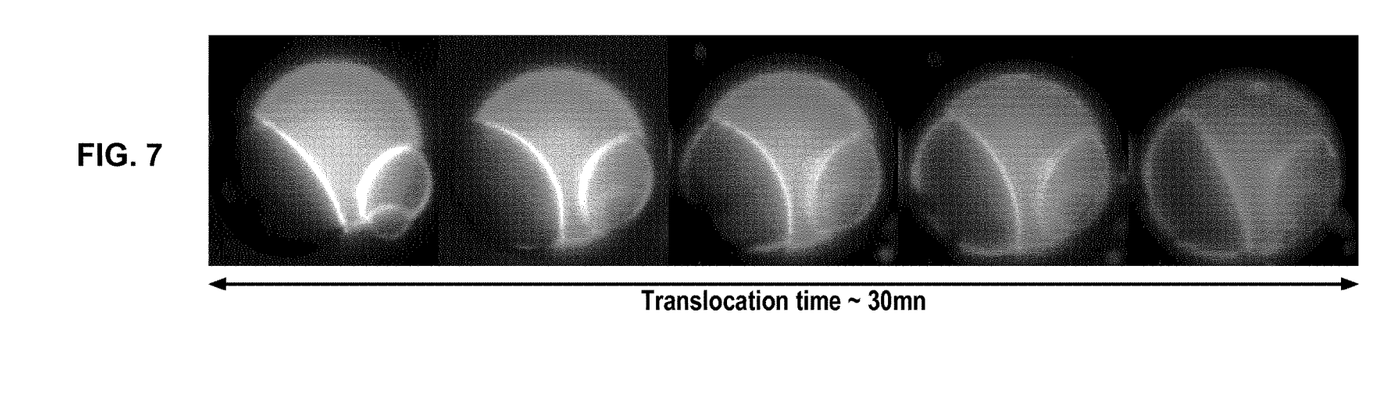
FIG. 7 represents photographs of a pair of droplets $D_1$ and $D_2$ during time (30 min), $D_1$ containing a fluorescent peptide which translocates to $D_2$.

When the emulsion is in a closed Lab-Tek™ chamber, the contact angle is small and no translocation is observed. When the lid of the Lab-Tek™ chamber is removed, chloroform evaporates and the contact angle increases (Thiam et al. *Langmuir* 2012, 28(15): 6291-6298)), corresponding to an increase of translocation. The results obtained are presented on FIG. 5 and on FIG. 6 showing the increase of translocation with the increase of the contact angle, as well as on FIG. 7 showing the evolution of translocation and thus fluorescence during time.

Figure 8:
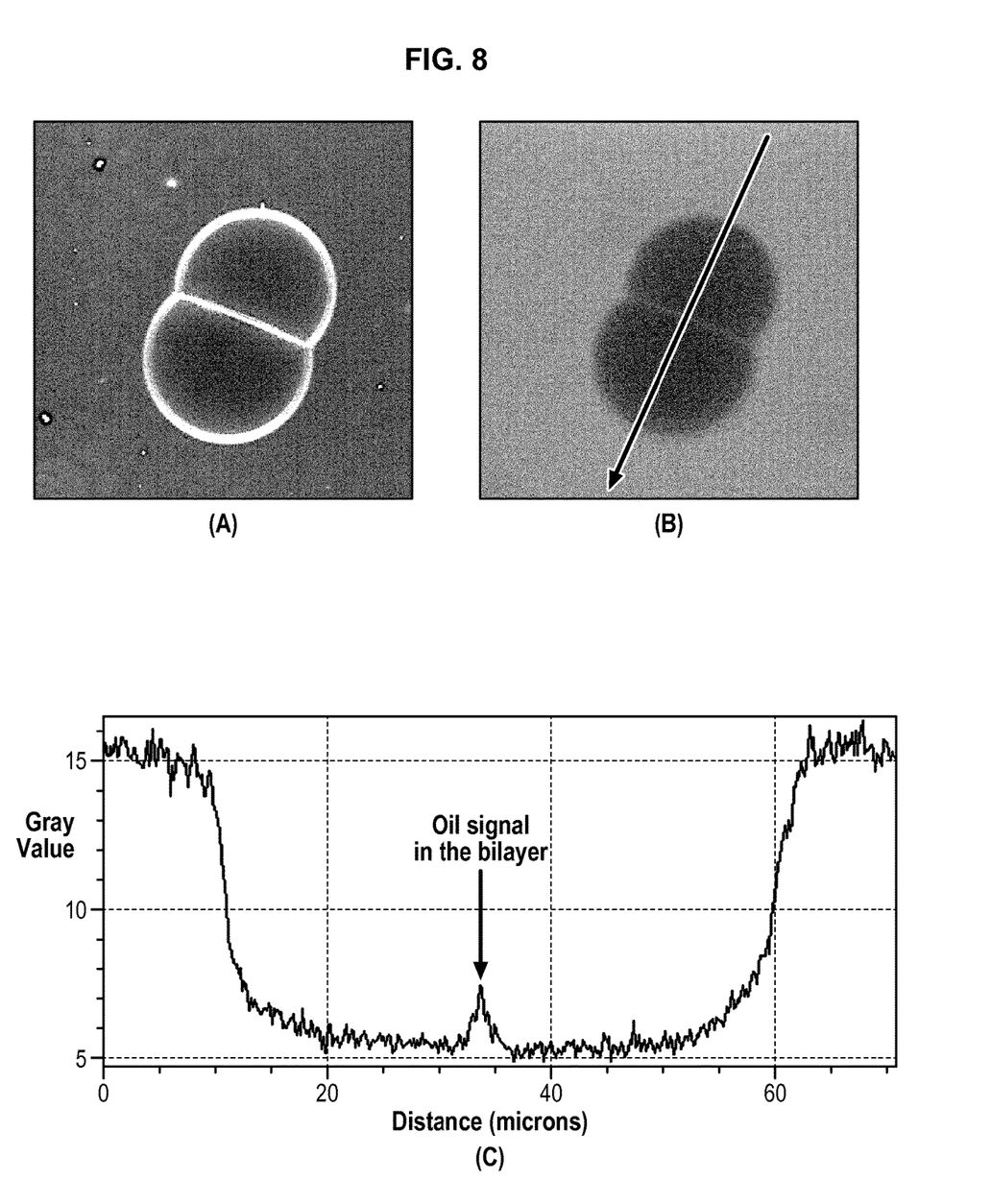
FIG. 8 represents, for a Droplet Interface Bilayer (DIB) having a low contact angle: (A) the fluorescent image of rhodamine-PE contained in the DIB in order to visualize the phospholipid layers, (B) the fluorescent image of triolein-pyrene contained in the hydrophobic medium in order to visualize the hydrophobic medium, and (C) the oil signal (gray value) measured along the arrow showing the presence of an oil signal in the phospholipid bilayer.
Figure 9:
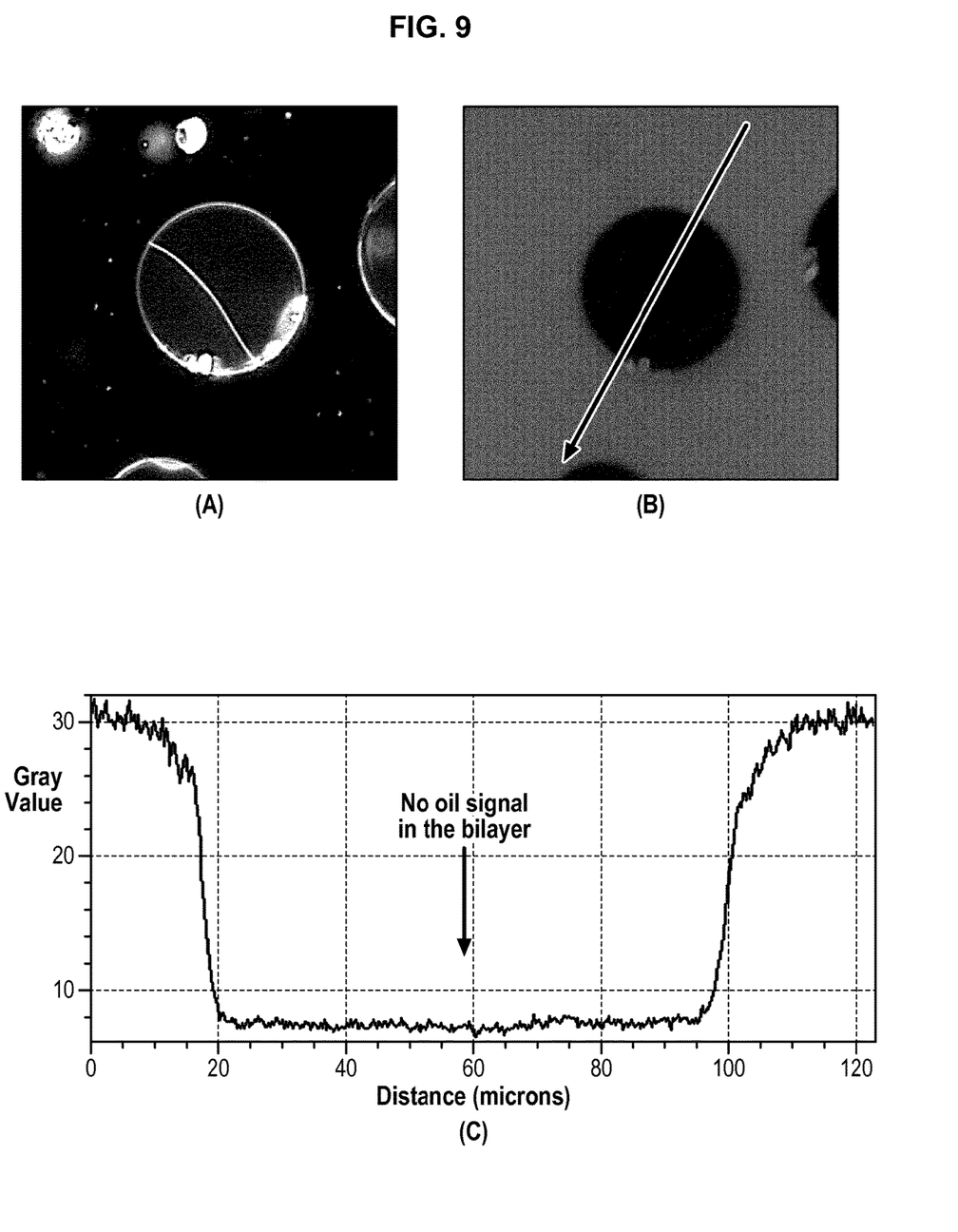
FIG. 9 represents, for a Droplet Interface Bilayer (DIB) having a high contact angle: (A) the fluorescent image of rhodamine-PE contained in the DIB in order to visualize the phospholipid layers, (B) the fluorescent image of triolein-pyrene contained in the hydrophobic medium in order to visualize the hydrophobic medium, and (C) the oil signal (gray value) measured along the arrow showing the absence of an oil signal in the phospholipid bilayer.

Using a fluorescent triolein (triolein containing 5% triolein-pyrene), we observed that for a DIB with a small contact angle obtained with DOPE containing 0.1 wt % of rhodamine-PE (fluorescent phospholipid) as phospholipids (the total phospholipids being present at 0.2 wt % in the oil, the concentration of rhodamine-PE in the oil is 0.0002 wt %), an oil film is present between the two layers of the phospholipid bilayer that contributes actually to the stability of the DIB. However, this oil film behaves also as a consequent barrier to cross for the peptide to translocate. Such an oil film is not present for a DIB with a high contact angle obtained with DOPC containing 0.1 wt % of rhodamine-PE. These results are presented on FIGS. 8 and 9.

The experiment was repeated without chloroform with a phospholipid mixture (final concentration being still 0.2% w/w to the oil with DOPC/DOPG/DOPE at 40/30/30 (w/w/w)) to have phospholipids favouring stability and translocation. We observe translocation of penetratin-gfp.

Figure 10:
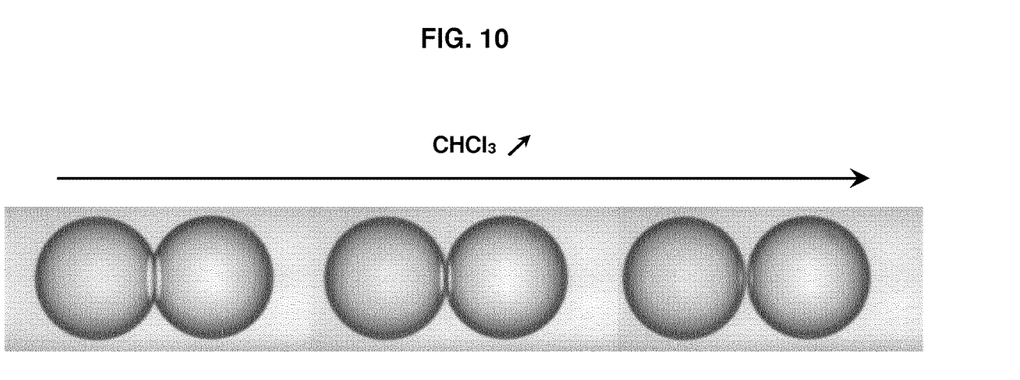
FIG. 10 represents photographs of a pair of droplets $D_1$ and $D_2$ during the progressive addition of chloroform to the hydrophobic medium.

The addition of chloroform to the hydrophobic medium allows separating the droplets as illustrated on FIG. 10 with the progressive addition of chloroform.

The invention claimed is:

1. A method to analyse the ability of a substance to cross a bilayer membrane comprising the following steps:
   (i) providing in a hydrophobic medium a first droplet $D_1$ of an aqueous solution $AS_1$, wherein the droplet $D_1$ is surrounded by a monolayer of amphiphilic molecules,
   (ii) providing in said hydrophobic medium a second droplet $D_2$ of an aqueous solution $AS_2$ containing the substance to be analysed, wherein the droplet $D_2$ is surrounded by a monolayer of amphiphilic molecules,
   (iii) putting the first droplet $D_1$ and the second droplet $D_2$ into contact so as to form a bilayer of amphiphilic molecules in the contact area and to have a contact angle $2\theta$ between the two droplets $D_1$ and $D_2$ comprised between 90° and 180°,
   (iv) adding to the hydrophobic medium a solvent capable of separating the droplets $D_1$ and $D_2$ put into contact, wherein the solvent capable of separating the droplets $D_1$ and $D_2$ put into contact is selected from the group consisting of a halogenated hydrocarbon, an alcohol, an ether, a fatty acid, a diglyceride, an ester, a low molecular weight hydrocarbon, and a mixture thereof,
   (v) collecting the droplet $D_1$, and
   (vi) analysing the content of the droplet $D_1$ in order to determine the presence or not of the substance,
      wherein the halogenated hydrocarbon is a linear or branched, saturated or unsaturated hydrocarbon comprising 1 to 6 carbon atoms, in which one or more hydrogen atoms have been replaced by a halogen atom,
      wherein the alcohol is a linear or branched, saturated or unsaturated hydrocarbon comprising 1 to 12 carbon atoms, in which a hydrogen atom has been replaced with an OH group,
      wherein the ether is a molecule of formula $A_4$—O—$A_5$, wherein $A_4$ and $A_5$ each represent independently of one another a monovalent linear or branched, saturated or unsaturated hydrocarbon chain comprising 1 to 12 carbon atoms, or $A_4$ and $A_5$ form together a divalent linear or branched, saturated or unsaturated hydrocarbon chain comprising 1 to 12 carbon atoms and optionally containing another oxygen atom,
      wherein the fatty acid is a linear, saturated or unsaturated carboxylic acid comprising from 4 to 18 carbon atoms,
      wherein the diglyceride is an ester derived from glycerol and two fatty acids which are identical or different,
      wherein the ester is a molecule of formula $A_7$—OC(O)—$A_8$, wherein $A_7$ and $A_8$ each represent independently of one another a monovalent linear or branched, saturated or unsaturated hydrocarbon chain comprising 1 to 12 carbon atoms, and
      wherein the low molecular weight hydrocarbon is a linear, branched or cyclic, saturated or unsaturated hydrocarbon containing no more than 9 carbon atoms.

2. The method according to claim 1, wherein the hydrophobic medium is an oil, triglycerides, a silicone oil, a high molecular weight hydrocarbon or a mixture thereof;
   optionally in admixture with a solvent selected from a halogenated hydrocarbon, an alcohol, an ether, a fatty acid, a diglyceride, an ester, a low molecular weight hydrocarbon and a mixture thereof.

3. The method according to claim 1, wherein the amphiphilic molecules are phospholipids, glycolipids, monoglycerides, cholesterol, or a mixture thereof.

4. The method according to claim 3, wherein the amphiphilic molecules are phospholipids.

5. The method according to claim 4, wherein the amphiphilic molecules are selected from dioleoylphosphatidylcholine (DOPC), dipalmitoylphosphatidylcholine (DPPC), dioleoylphosphatidylethanolamine (DOPE), dioleoylphosphatidylserine (DOPS), dioleoylphosphatidylglycerol (DOPG), and mixtures thereof.

6. The method according to claim 1, wherein the aqueous solutions $AS_1$ and $AS_2$ contain a buffering agent.

7. The method according to claim 1, wherein the first and second droplets $D_1$ and $D_2$ have a diameter comprised between 0.5 µm and 1000 µm.

8. The method according to claim 1, wherein step (i) is performed by:
providing the aqueous solution $AS_1$,
providing the hydrophobic medium further containing the amphiphilic molecules, and
forming a droplet of the aqueous solution $AS_1$ in the hydrophobic medium which contains the amphiphilic molecules.

9. The method according to claim 1, wherein step (ii) is performed by:
providing the aqueous solution $AS_2$ containing the substance,
providing the hydrophobic medium further containing the amphiphilic molecules, and
forming a droplet of the aqueous solution $AS_2$ containing the substance in the hydrophobic medium which contains the amphiphilic molecules.

10. The method according to claim 1, wherein the contact angle 2θ is comprised between 120° and 180°.

11. The method according to claim 1, wherein the droplets $D_1$ and $D_2$ are maintained into contact in step (iii) during at least 1 min.

12. The method according to claim 1, wherein step (vi) is performed by means of fluorescence imaging, HPLC or mass spectrometry.

13. The method according to claim 1, used in high-throughput.

14. The method according to claim 1, performed by means of a microfluidic analysis system comprising:
a microfluidic device comprising:
a first microfluidic channel comprising one inlet and one outlet, through which alternate droplets $D_1$ and $D_2$ can flow in the hydrophobic medium from the inlet to the outlet of the first microfluidic channel and can be put into contact,
a second microfluidic channel comprising one inlet and one outlet, through which the droplets $D_1$ and $D_2$ can flow in the hydrophobic medium from the inlet to the outlet of the second microfluidic channel and the droplets $D_1$ and $D_2$ put into contact can be separated, the inlet of the second microfluidic channel being connected to the outlet of the first microfluidic channel,
at least two outlets connected to the outlet of the second microfluidic channel, wherein:
the first outlet of the microfluidic device is further connected to a first receiver container intended to receive the droplets $D_1$ to be analysed, and
the second outlet of the microfluidic device is further connected to a second receiver container intended to receive the droplets $D_2$,
at least five inlets:
wherein four inlets of the microfluidic device are connected to the inlet of the first microfluidic channel,
the first two inlets being further connected respectively to a reservoir intended to contain the aqueous solution $AS_1$ and to a reservoir intended to contain the hydrophobic medium and the amphiphilic molecules, and
the last two inlets being further connected respectively to a reservoir intended to contain the aqueous solution $AS_2$ and the substance and to a reservoir intended to contain the hydrophobic medium and the amphiphilic molecules, and
wherein one inlet of the microfluidic device is connected to the inlet of the second microfluidic channel and is further connected to a reservoir intended to contain the solvent capable of separating the droplets $D_1$ and $D_2$ put into contact,
at least four reservoirs adapted for containing respectively (i) the aqueous solution $AS_1$, (ii) the aqueous solution $AS_2$ and the substance, (iii) the hydrophobic medium and the amphiphilic molecules, and (iv) the solvent capable of separating the droplets $D_1$ and $D_2$ put into contact,
at least two receiver containers adapted for receiving respectively (i) the droplets $D_1$ to be analyzed, and (ii) the droplets $D_2$, and
an analyzing device to analyze the content of droplets $D_1$.

15. The method according to claim 4, wherein the amphiphilic molecules are phosphatidylcholines (PC), phosphatidylethanolamines (PE), dioleoylphosphatidylglycerol (PG), dioleoylphosphatidylserine (DOPS), or a mixture thereof.

16. The method according to claim 7, wherein the first and second droplets $D_1$ and $D_2$ have a diameter comprised between 50 µm and 200 µm.

17. The method according to claim 11, wherein the droplets $D_1$ and $D_2$ are maintained into contact in step (iii) between 10 and 30 min.

18. The method according to claim 1, wherein the solvent capable of separating the droplets $D_1$ and $D_2$ put into contact is selected from chloroform, dichloromethane, butanol, diethyl ether, 1,4-dioxane, oleic acid, glyceryl dioctanoate, glyceryl dioleate, ethyl acetate, isopropyl acetate, pentane, cyclopentane, hexane, cyclohexane, benzene, toluene, and a mixture thereof.

19. The method according to claim 18, wherein the solvent capable of separating the droplets $D_1$ and $D_2$ put into contact is chloroform.

* * * * *